United States Patent
Tsang et al.

(10) Patent No.: US 6,817,754 B2
(45) Date of Patent: Nov. 16, 2004

(54) FUEL FREEZING POINT MONITORING DEVICE

(76) Inventors: Charles Tsang, 475 - West 28$^{th}$ Ave., Vancouver, British Columbia (CA), V5Y 2K9; Gordon S. Y. Chiu, 11271 Daniels Road, Richmond, British Columbia (CA), V6X 1M5

( * ) Notice: Subject to any disclaimer, the term of this patent is extended or adjusted under 35 U.S.C. 154(b) by 11 days.

(21) Appl. No.: 10/123,915

(22) Filed: Apr. 16, 2002

(65) Prior Publication Data

US 2003/0193989 A1 Oct. 16, 2003

(51) Int. Cl.$^7$ .............................................. G01N 25/04
(52) U.S. Cl. .......................... 374/20; 374/144; 374/147
(58) Field of Search ................................ 374/16–20, 25, 374/141, 144, 147; 73/61.41, 64.43, 64.56, 118.1; 356/70, 440, 442, 947; 123/494; 116/216

(56) References Cited

U.S. PATENT DOCUMENTS

| | | | |
|---|---|---|---|
| 2,635,455 A | 4/1953 | Staehling | 374/25 |
| 3,077,764 A * | 2/1963 | Kapff | 374/19 |
| 3,187,577 A * | 6/1965 | Scherer | 60/527 |
| 3,527,082 A | 9/1970 | Pruvot et al. | 374/17 |
| 3,818,614 A | 6/1974 | Meurer | 374/17 |
| 4,321,136 A | 3/1982 | Matsui | 210/86 |
| 4,705,100 A | 11/1987 | Black et al. | |
| 4,760,538 A | 7/1988 | Bock et al. | 374/25 |
| 4,804,274 A | 2/1989 | Green | |
| 4,807,584 A | 2/1989 | Davis | 123/557 |
| 4,886,354 A | 12/1989 | Welch et al. | 356/70 |
| 5,090,817 A | 2/1992 | Ker et al. | 374/16 |
| 5,141,329 A | 8/1992 | Orlando et al. | 374/25 |
| 5,282,682 A | 2/1994 | Orlando et al. | |
| 5,651,614 A | 7/1997 | Juneau | 374/17 |
| 5,654,497 A | 8/1997 | Hoffheims et al. | |
| 5,754,055 A | 5/1998 | McAdoo et al. | |

* cited by examiner

*Primary Examiner*—Edward Lefkowitz
*Assistant Examiner*—Stanley J. Pruchnic, Jr.
(74) *Attorney, Agent, or Firm*—John J. Elnitski, Jr.

(57) ABSTRACT

A fuel freezing point monitoring device to monitor the freezing point of onboard fuel, especially aircraft fuel. The fuel freezing point monitoring device is capable of monitoring the phase transition or fluidity of the fuel to determine the freezing point of the fuel. The fuel freezing point monitoring device eliminates the freezing point assumption of onboard fuel by actually measuring the freezing point of the fuel. The pilot will have knowledge of the approximate freezing point of the composite onboard fuel and will no longer need to assume a conservative fuel freezing point value. Together with the en-route fuel temperature information provided by existing aircraft sensors, the pilot will have the information to ensure a safe flight and to operate the aircraft efficiently.

40 Claims, 5 Drawing Sheets

FUEL FREEZING POINT MONITORING DEVICE

BACKGROUND

The present invention generally relates monitoring the freezing temperature of fuel onboard a vehicle. More specifically, the present invention relates to monitoring the freezing point of jet fuel onboard an aircraft.

In recent years, Russia officially opened Russian airspace to commercial airlines and flight routes over the North Pole are available for use. An era of commercial transpolar flight has begun, offering an unprecedented efficient and economic link between cities of North America, Asia and Europe. The polar routes are extremely attractive to the airlines and their customers for many reasons, the paramount of which being faster non-stop services between such major centers as New York and Hong Kong, cutting up to six hours off regular travel time. For the first time, airlines can offer faster, possibly cheaper, flights between the world's most important business centers. Not only is non-stop service highly attractive for the travel-weary customer, there are also numerous benefits for the airlines. In addition to significant fuel savings and reduced amount of operation time and labor cost, there is the further benefit of a smoother flight due to a lack of headwinds along these routes during the winter months.

With any significant change in flight operations, a thorough review of the technical challenges involved and their possible impact on aircraft safety is critical. With polar flights, there are two particular issues related to the freezing point of the jet fuel on the aircraft. Should the jet fuel in the wing tanks reach its freezing point, there is a possibility of the following: (1) The flow of fuel to the engine becomes blocked, causing the engine to stutter and, possibly, loss of the aircraft; or (2) the fuel solidifies and becomes trapped within tanks, curtailing the amount of useful fuel available to the engine. Certainly, the scenario of fuel freezing has always been an important consideration, even for regular flights. However, with polar flight, this issue is heightened as the aircraft is often flying in outside ambient temperatures that can commonly reach minus seventy degrees Celsius (−70° C.) or colder. Flying over the North Pole's large permafrost and the drastic reduction in sunlight during the winter months means an increase in the possibility of fuel in the wing tanks reaching its freezing point. All outbound aircraft in the US are dispatched with Jet A fuel, with a specification freezing point of −40° C. With no means of testing the fuel as it is being uploaded to each aircraft, the pilot must fly assuming that the freezing point of the fuel in the aircraft is −40° C. as specified.

Various published studies have confirmed that the fuel temperature in the wing tanks of about fifty percent (50%) of certain scheduled polar flights fall to within 3° C. above freezing point specification. This amount of cooling in the fuel is significant for most aircrafts, as pilots are directed to perform mandatory corrective measures to warm the fuel, if and whenever the fuel temperature falls to −37° C. These measures include increasing aircraft speed, descending to a lower altitude and/or maneuvering around the cold-air cell. Aside from the fact that pilots prefer to avoid any change in flight operations, these corrective measures result in significant expenses for the airlines. Therefore, the benefits of flying polar, such as less time less fuel and smoother flight, will not be fully realized. However, a survey of seven major gateway airports in the US has demonstrated that the fuel being uploaded into each aircraft often has a lower freezing point then the required −40° C. If this freezing point temperature can be certified, many of the corrective actions described above could be rendered unnecessary.

In the absence of an onboard system, the safety of an aircraft flying a long-range polar route must depend on the knowledge of the fuel temperature during flight, coupled with the assumption of the fuel freezing point. If the assumption is conservative, which is often the case, the aircraft is inefficiently operated because of the many unnecessary "corrective actions". If the unexpected scenario occurs of the actual freezing point of the fuel being warmer than the specification value, the outcome could be catastrophic. It should be noted that ground-based freezing point analyzers have been available for quite some time. However, these ground-based analyzers lack the ability to collect a representative sample inside the aircraft fuel tank. These ground-based analyzers can at best monitor the freezing point of the fuel being loaded into the fuel tank, but frequently the pilot is more interested in the freezing point of the composite fuel that is onboard the aircraft and being delivered to the engines during flight. The composite fuel is made up of the fuel from the current fill as well as residual fuels in the aircraft tanks that originated from previous airports. Since the amount and chemical composition of residual fuel vary, and the mixing of fuels is not uniform inside the multiple fuel tanks that are separated by baffles, it is impossible to predict or correlate the freezing point of the composite fuel based on information generated by ground-based freezing point analyzer. In fact, the freezing point of the composite fuel could be different from that measured by the ground-based analyzer by up to several degrees Celsius. This amount of difference is often sufficiently important to decide whether corrective action should or should not be taken.

In order to incorporate a fuel analyzer into an aircraft, there are important restrictions to be satisfied. These restrictions are often not considered or applicable for ground-based systems. For instance, space is in short supply in the aircraft in general and particularly in the fuel tank area, the size and weight of the device becomes a key issue. Equally important is the manner in which the device is implemented due to its proximity to a large amount of highly flammable material. There are other requirements for aircraft-mounted device that ground-based instruments cannot readily satisfy. For example, aircraft-mounted device must have a minimum demand on utilities as they are not conveniently available. Some ground-based systems require the consumption of liquid carbon dioxide for cooling or the consumption of dry and compressed nitrogen for purging and cooling. However, liquid carbon dioxide and compressed nitrogen are disallowed in aircraft because of high pressure storage requirement and because both are asphyxiants. Moreover, an aircraft-mounted device must be rugged enough to withstand vibrational shocks that could take place during unusual situations such as extreme turbulence or loss of function of an engine. Wherein, some ground-based systems require multiple pieces of delicate glassware, some of which are double-walled to hold the fuel sample and coolant. Such delicate apparatus would not be very suitable for a mounting inside an aircraft.

It is an object of the present invention to provide a device useable in an aircraft that is capable of determining the freezing point of fuels so that flights vulnerable to enroute low temperature fuel delivery problems could be conducted safely and efficiently.

SUMMARY

A fuel freezing point monitoring device having a test chamber with an internal channel for retaining a fuel sample.

There is input into said test chamber to allow input of the fuel sample. There is an output out of said test chamber to allow exiting of the fuel sample. There is a cooler in thermal contact with said test chamber for cooling the fuel sample in said test chamber. There is a light transmission path along said internal channel having an entrance into said test chamber and an exit out of said test chamber. There is a light source which directs light into said entrance of said light transmission path and a light detector to detect light level from said light source exiting said exit of said light transmission path.

DETAILED DESCRIPTION

The present invention is a fuel freezing point monitoring device. The fuel freezing point monitoring device can be mounted in an aircraft to monitor the freezing point of onboard fuel. The fuel freezing point monitoring device is capable of monitoring the phase transition or fluidity of the aircraft fuel to determine the freezing point of the fuel. When an external motive force, such as pump or gravity drain, is not available, the fuel freezing point monitoring device can also include a means to assist in delivering a fuel sample from an aircraft fuel source to the fuel freezing point monitoring device. The fuel freezing point monitoring device eliminates the freezing point assumption of onboard fuel by actually measuring the freezing point of the fuel. The pilot will have knowledge of the approximate freezing point of the composite onboard fuel and will no longer need to assume a conservative fuel freezing point value. Together with the en-route fuel temperature information provided by existing aircraft sensors, the pilot will have the information to ensure a safe flight and to operate the aircraft efficiently.

As is a requirement for most onboard equipment of an aircraft, the fuel freezing point monitoring device should be small, lightweight and avoid the use of dangerous liquids or gases. It is desirable to mount the fuel freezing point monitoring device next to or close to an aircraft fuel tank. Where there is concern over the freezing point of fuel in separate fuel tanks, it may be beneficial to have a manifold to allow fuel from active tanks to enter one fuel freezing point monitoring device, or incorporate the fuel freezing point monitoring device into a hand-held device that can be conveniently attached and detached to suitable nodes for the purpose of fuel analysis. In doing so, the complexity and costs involved in equipping each fuel tank with a dedicated fuel freezing point monitoring device can be avoided. The following embodiments consider all the above-mentioned concerns with equipment to be used onboard an aircraft.

Figure 1:
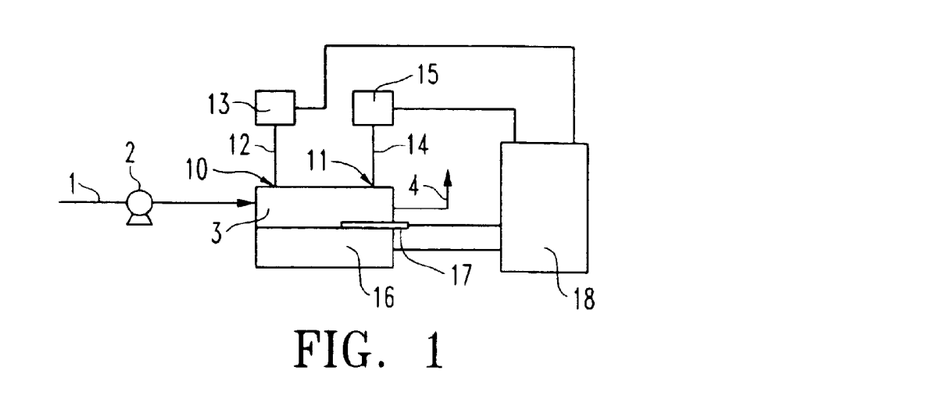
FIG. 1 is a schematic of the basic concept according to the present invention.

FIG. 1 shows the basic concept employed in all setups of the fuel freezing point monitoring device to be further disclosed. A jet fuel sample 1 from an aircraft fuel tank is delivered into an internal channel of a light-leak-proof and thermally conductive test chamber 3. The configuration of the test chamber 3 is the main difference in all the setups to be further disclosed. A pump 2 is shown as an example of a means of transferring the fuel sample 1 to the fuel freezing point monitoring device. A sufficient amount of fuel sample 1 is needed to completely fill the test chamber 3 and purge the test chamber 3 of any residual fuel sample remaining from a previous test. Excess fuel from the test chamber 3 is returned through a drain tube 4 to either a fuel tank or a sump. Once the test chamber 3 is completely filled with the new fuel sample 1, the flow into the test chamber 3 is halted. The fuel freezing point monitoring device includes a light emitter 13 as a light source and a light detection unit 15 for monitoring light levels. The light emitter 13 and light detection unit 15 are light devices that interact in combination with the test chamber 3 to provide a beam of light through the fuel sample 1. The test chamber 3 is in thermal contact with a surface that is chilled by a cooler 16, so that the fuel sample 1 can be cooled. A temperature sensor 17 is embedded in the test chamber 3 in close proximity to the fuel sample 1. A data acquisition and control unit 18 is used to control the cooling and warming rates of the fuel sample 1; to collect information from the temperature sensor 17 and from the light detection unit 15; and to analyze the collected data. A microprocessor equipped with the necessary software and hardware is utilized as part of the data acquisition and control unit 18.

Light from the light emitter 13 is passed through the fuel sample 1 in the test chamber 3 and onto the light detection unit 15, along what is considered a light transmission path 103 in the test chamber 3. The light is usually in the form of a controlled beam of light. To determine freezing point of a particular source of fuel onboard the aircraft, the fuel sample 1 within the test chamber 3 is cooled until crystals are formed. The fuel sample 1 is then warmed until all crystals have melted. According to the test method established by the American Society of Testing and Materials (ASTM), the temperature at which the last crystals disappear is defined as the freezing point of the fuel. The fuel can be warmed by reducing the cooling applied to the test chamber by the cooler 16 or by having an additional warming device to apply heat to the test chamber 3. In most cases, a warming device will not be used to save on weight and complexity of the fuel freezing point monitoring device. When light from the light emitter 13 is passed through the fuel sample 1 in the test chamber 3 and onto the light detection unit 15, the light will scatter beyond its normal light transmission path 103 when there are crystals present in the fuel sample 13. The scattering of the light will reduce the level of light that the light detection unit 15 detects, as compared to when there are no crystals present. So, the fuel sample 1 is cooled to form crystals and warmed until the last crystal created melts, whereby the data acquisition and control unit 18 records the temperature in the test chamber 3 where the light level no longer increases during warming. This recorded temperature is the freezing point of the fuel sample 1. The following describes different setups for the test chamber 3, light emitter 13 and light detection unit 15 used as part of the fuel freezing point monitoring device. Very often, the design of the test chamber 3 using the basic concept is constrained by the cooling surface area and cooling capacity available from the cooler 16. Given these constraints and the objective to maximize signal differentiation at the freezing point in a limited spaced vehicle, the construction of the test chamber 3 must allow for as much fuel sample into the test chamber 3 as possible. Of equal importance, the construction of the test chamber 3 must allow for as long a light transmission path 103 as possible. It is believed a good range of distance that the light should travel along the normal light transmission path 103 in the test chamber 3 is about 10–30 millimeters so as to provide sufficient signal contrast for freezing point measurement. All of the setups described implement the above basic concept of FIG. 1 in a unit that meets the equipment requirements of today's aircraft.

Figure 2:
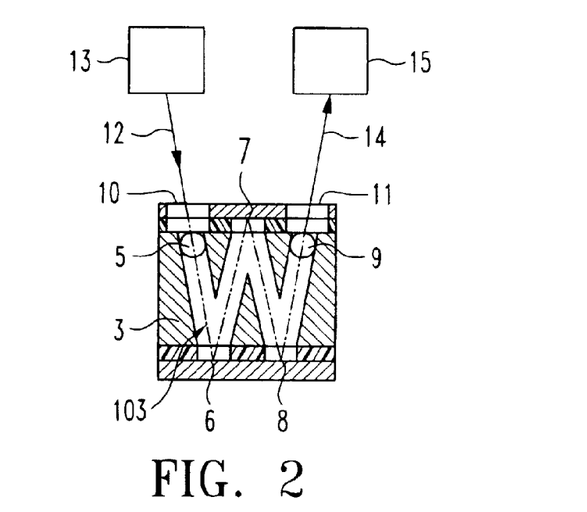
FIG. 2 is a cross-sectional view of a test chamber according to the present invention.
Figure 3:
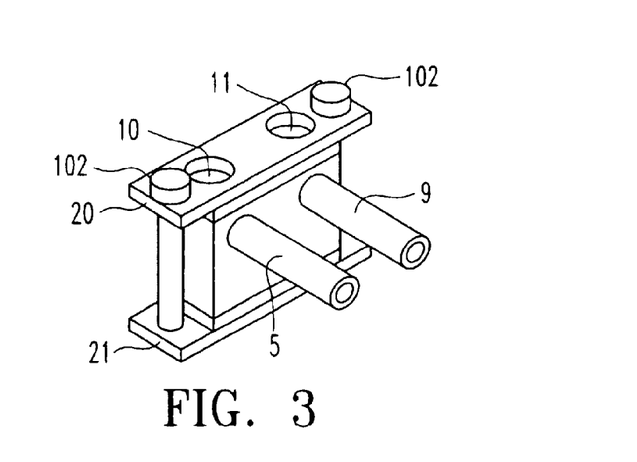
FIG. 3 is a perspective view of the test chamber of FIG. 2 according to the present invention.

FIGS. 2–3 show a test chamber 3 in a setup having an internal channel and light transmission path 103 along path points 10, 6, 7, 8, 11 in the shape of the letter "W". In the setup of FIGS. 2–3, the fuel sample enters the test chamber 3 from an inlet 5 and flows along the light transmission path 103 in the horizontal x-y plane defined by path points 6, 7, 8, before exiting the test chamber 3 at an outlet 9. A light transmission device 12 transmits light from the light emitter 13 directly into the test chamber 3 at one of the shown transparent ports 10 or 11 of the "W" path. As an example, a fiber-optic light cable could be used as the light transmission device 12. FIG. 2 shows the light from the light transmission device 12 entering the transparent port 10. The light transmission device 12 is used to direct the light into the transparent port 10. Reflective surfaces are placed at path points 6, 7, 8 where the light transmission path 103 of the test chamber 3 changes direction. In this way, the beam of light follows the entire "W" path and emerges at the other transparent port 11. Another light transmission device 14 transfers the light from the test chamber and onto the light detection unit 15. In the setup of FIGS. 2–3, crystal formation within the test chamber 3 causes the light to scatter within the "W" light transmission path 103, thus diverting some of the light away from the normal light transmission path 103. Part of the scattered light is absorbed by the walls along the normal light transmission path 103; as a result, the light detection unit 15 at the transparent port 11 receives a reduced level of light. Since it is important to keep the test chamber 3 small, all the components of the test chamber 3 must be miniaturized. For example, the test chamber 3 of FIGS. 2–3 can be approximately 1 cm square by 0.3 cm thick. The diameter of the light transmission path 103 can be approximately 0.2 cm. A thermally conductive material such as copper or aluminum may be used for the construction of the test chamber 3, so that the test chamber 3 is easily cooled by the cooler 16. The reflective surfaces at path points 6, 7, 8 are provided by the end plates 20 and 21 shown in FIG. 3. These end plates 20, 21 can be chromed or polished to provide a highly reflective surface. Bolts 102 are shown in FIG. 3 and hold the end plates 20, 21, as well, as the other components of the test chamber 3 together. By reducing the overall dimension of the test chamber 3, the thermal mass of the test chamber 3 is decreased, hence allowing the use of a small cooler 16. Miniaturized coolers such as Stirling, pulse-tube, or thermoelectric can be used. The "W" path configuration is one way to maximize fuel sample volume and light transmission path 103 length within a limited cooling space.

Figure 4:
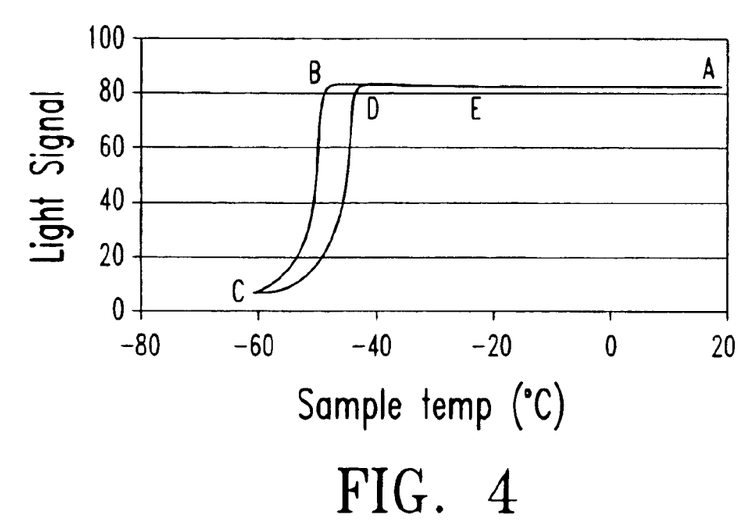
FIG. 4 is plot of light intensity and temperature for the test chamber of FIG. 2 according to the present invention.

FIG. 4 is a graphical plot of results obtained in a typical freezing point test obtained by the setup of FIGS. 2–3. The test began at "A" when the fuel sample was at room temperature. The light received by the light detection unit 15 was at a high level due the lack of obstruction along the "W" transmission path. As the fuel sample was chilled, the light level remained high until crystals were formed at "B". The formation of crystals caused the transmitted light level to drop sharply between "B to C". The subsequent warming of the fuel sample resulted in melting of the crystals and a proportional increase in transmitted light occurred between "C to D". Eventually, all the crystals melted at "D" and further warming did not result in a change in transmitted light level between "D to E". The temperature at which the last crystals disappear at "D" is recorded as the freezing point of the fuel sample.

Figure 5:
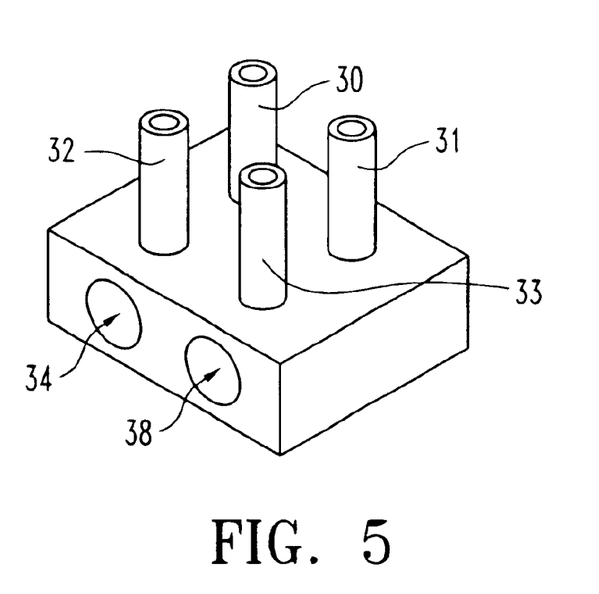
FIG. 5 is a perspective view of another test chamber according to the present invention.
Figure 6:
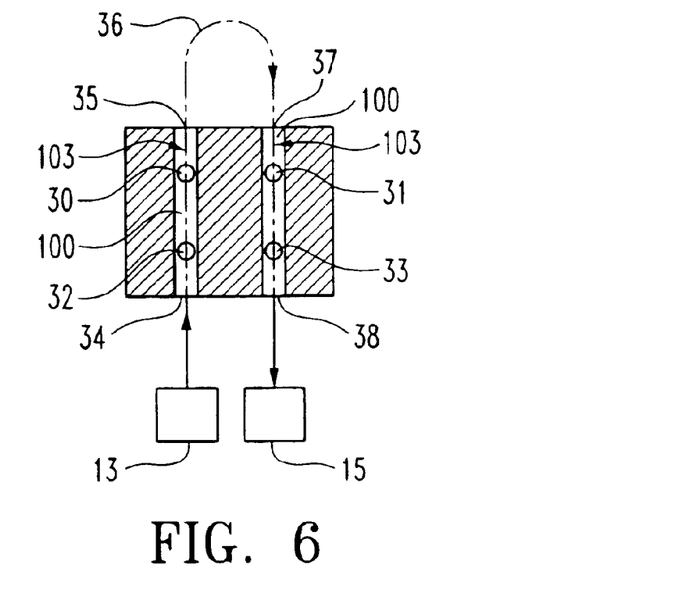
FIG. 6 is a cross-sectional view of the test chamber of FIG. 5 according to the present invention.

FIGS. 5–6 show another setup using the basic concept in which there are two parallel internal channels 100. The fuel sample enters the test chamber 3 through inputs 30 and 31 and exits through outputs 32 and 33. Light from the light emitter 13 enters the test chamber 3 through transparent port 34, through channel 100 and travels on out of transparent port 35. A light transmission device 36 is used to transfer the light from transparent port 35 to transparent port 37. The light continues its travel from transparent port 37, through channel 100 and on out of transparent port 38, where the light detection unit 15 is positioned. In the "W" design of FIGS. 2–3, reflectors are used to divert light from one straight channel to another; whereas in the setup shown in FIGS. 5–6, the diversion is facilitated with the light transmission device 36. The number of channels shown in FIGS. 5–6 may be increased or decreased and the number of light optical light guides accordingly multiplied or reduced to increase or decrease the degree of redundancy.

Figure 7:
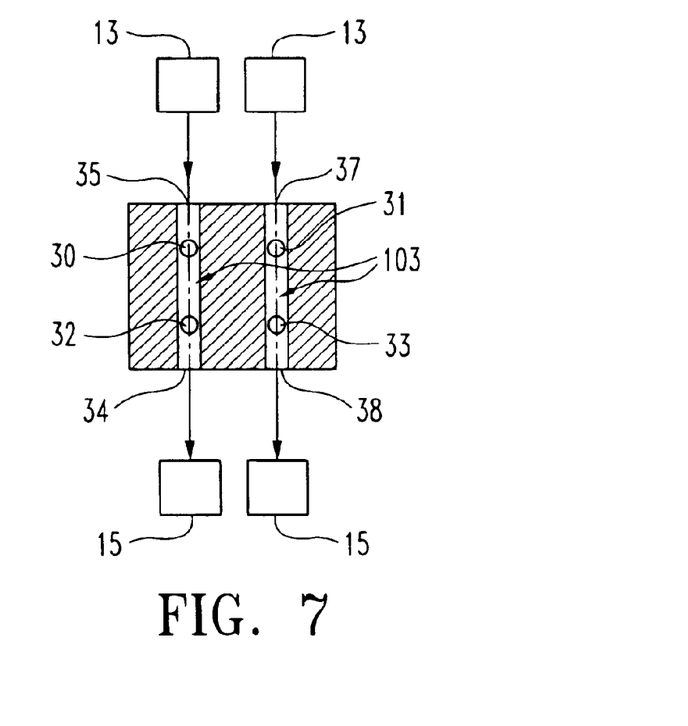
FIG. 7 is a cross-sectional view of the test chamber of FIG. 5 according to the present invention.

FIG. 7 shows a different way of using the test chamber 3 of FIGS. 5–6, by employing more than one light emitter 13 and light detection unit 15 combination. This adds redundancy to the fuel freezing point monitoring device. Whereby, transparent ports 35 and 37 can be illuminated by separate light emitters 13 and transparent ports 34 and 38 are monitored by separate light detection units 15. Therefore, two independent freezing point measurements can be made simultaneously, whereby there is a freezing point value from each channel 100. In the event that one of the light emitters 13 or light detection units 15 fail, the fuel freezing point monitoring device can still function and provide freezing point data. Again, the number of independent channels 100 in the test chamber 3 along with associated light emitters 13 and light detection units 15 may be increased beyond two to increase redundancy.

Figure 8:
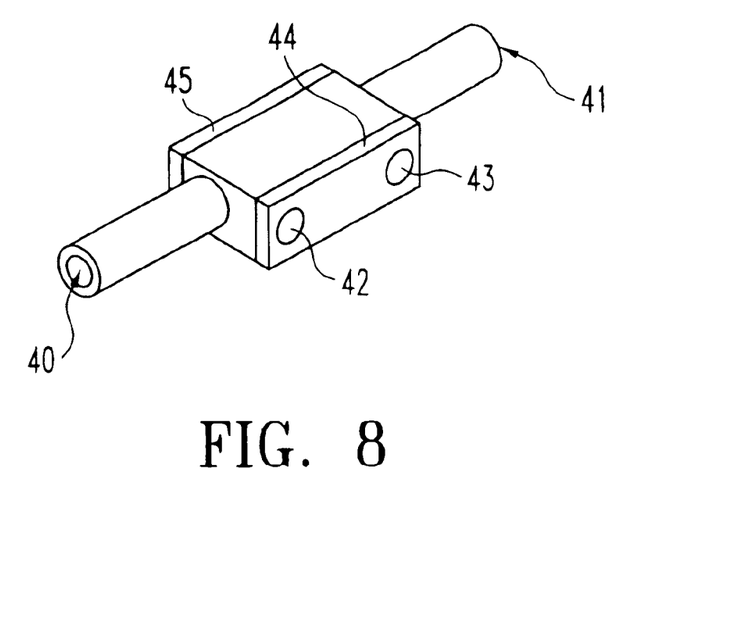
FIG. 8 is a perspective view of another test chamber according to the present invention.
Figure 9:
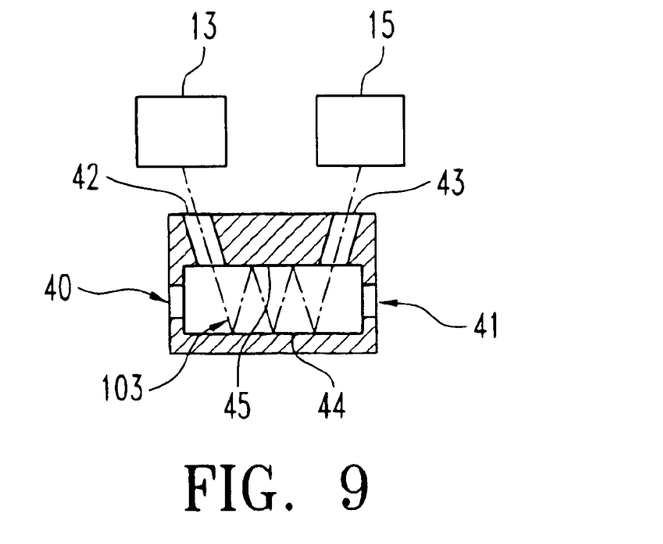
FIG. 9 is a cross-sectional view of the test chamber of FIG. 8 according to the present invention.

FIGS. 8–9 show another test chamber 3 setup, in which the length of the light transmission path 103 in a straight internal channel is maximized through multiple reflections between two parallel, reflective surfaces. The fuel sample enters inlet 40 into a straight-line internal channel and exits through output 41. Light from the light emitter 13 is directed into the fuel sample through transparent port 42 at an acute angle. Upon impinging on the reflective surface at the bottom 45 of the test chamber 3, the light is reflected upward and subsequently impinges on the top reflective surface 44. This reflection process is repeated until the light finally emerges from transparent port 43, at the other end of the test chamber 3. In designing the test chamber 3 of FIGS. 8–9, the number of reflections can be adjusted by the angle of impingement and the distance between the two parallel, reflective surfaces 44, 45. The test chamber 3 of FIGS. 8–9 uses a simple linear internal channel similar to the one shown in FIGS. 5–7, but converts a shorter linear light transmission path 103 into a considerably longer light transmission path 103 that resembles a "saw tooth" pattern. The longer light transmission path 103 provides better sensitivity in detecting the appearance and disappearance of crystals.

Figure 10:
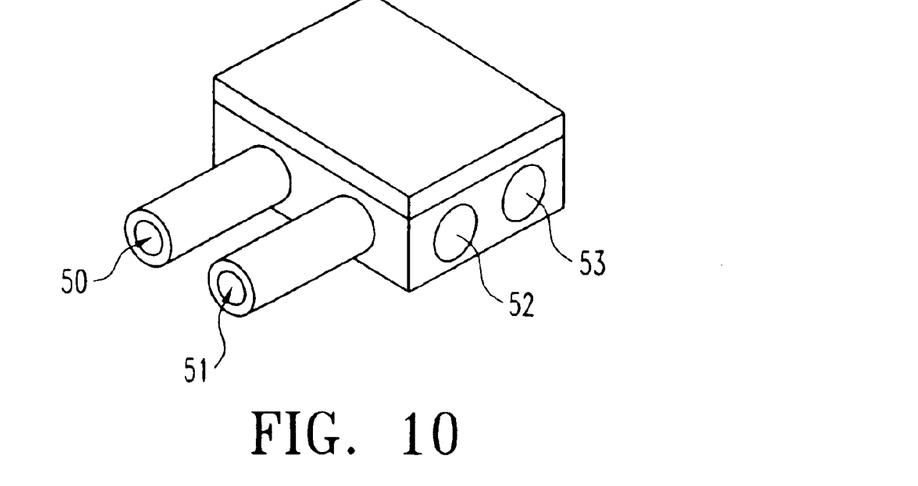
FIG. 10 is a perspective view of another test chamber according to the present invention.
Figure 11:
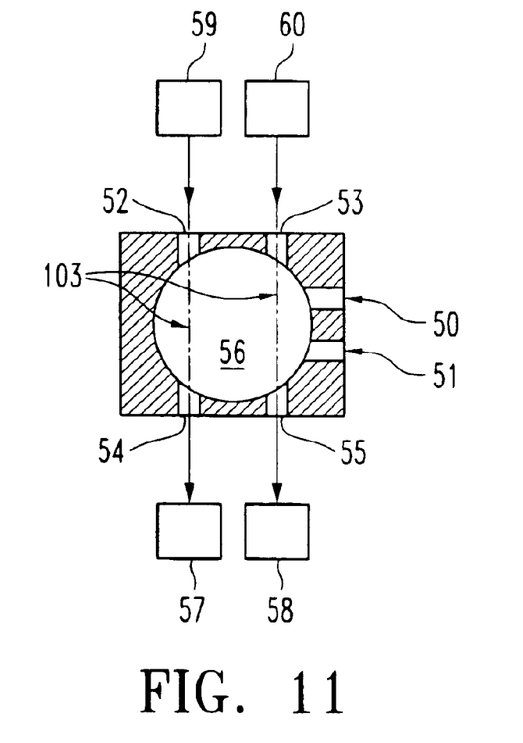
FIG. 11 is a cross-sectional view of the test chamber of FIG. 10 according to the present invention.

FIGS. 10–11 show another setup of the test chamber 3, which includes the ability to provide redundancy for the beam of light and its detection. The fuel sample enters the test chamber 3 through input 50 and exits through output 51. The internal channel 56 is shaped like a flat circular disc. Light from the light emitter 59 enters the internal channel 56 through the transparent port 52 and the transmitted light leaves the internal channel 56 through transparent port 54, that is positioned opposite from and in alignment with the light emitter 59 and forms a light transmission path 103. The light detector 57 is placed at transparent port 54 to capture the transmitted light from the light emitter 59. A second light detector 58 is positioned away from the straight-line path of the beam light originating from light emitter 59, but in a favorable forward scatter angular position associated with the nature of the hydrocarbon crystals in aircraft fuels. In the absence of crystals, light detector 57 receives a high intensity of light while the light detector 58 receives practically no light. Once the crystals are formed, part of light is scattered by the surface the crystals and thus light detector 57 receives a sharp reduction in light intensity. At the same time, the light detector 58 receives a marked increase in light intensity due to the occurrence of scattered light by the crystals. In this way, both light detectors 57, 58 are capable of detecting crystal appearance and disappearance, thus the freezing point can be validated. In the event one of the light detectors 57, 58 fails, the other can still continue to provide freezing point information.

To guard against the failure of the light emitter 59, an additional light emitter 60 can be placed at transparent port 53, which is opposite from and in alignment with transparent port 55. Redundancy is achieved by operating the light detectors 57, 58 and the light emitter 59 in the manner described above, until the light emitter 59 becomes non-functional. Then, the light emitter 60 is activated to replace the function of light emitter 59. In that event, light detector 58 will monitor transmitted light while light detector 57 will monitor scattered light. The switching of functions for the light emitters 59, 60 and light detectors 57, 58 can be executed by the data acquisition and control unit 18 of FIG. 1. Even greater flexibility is attained by activating light emitters 59 and 60 in alternate time sequence. For example, the light emitter 59 is first activated together with the light detector 57 in transmission mode and the light detector 58 in scattered mode. Once the light detectors 57, 58 have completed the collection of one data point, the light emitter 59 is turned off and the light emitter 60 is turned on together with the light detector 58 in transmission mode and the light detector 57 in scattered mode. This process of alternating the use of the light emitters 59 and 60 is repeated until a freezing point test is completed. Other methods of operating and positioning the light emitters 59, 60 and light detectors 57, 58 to achieve freezing point validation and redundancy are available and within the scope of the present invention.

It has been determined that the orientation of the test chamber and the light transmission path can affect the sensitivity of crystal detection. Since the crystals are denser than the liquid from which they are formed, the crystals tend to fall to the lowest point in the test chamber due to the force of gravity. By placing the test chamber so that the internal channel and hence the light transmission path is in a vertical position between the light devices, the crystals formed upon cooling fall toward the either the light emitter or the light detector at the bottom of the internal channel and cause a more effective blockage of light transmission. This is best illustrated by the orientations shown in FIGS. 6–7. FIG. 5 illustrates the test chamber and the internal channel in a horizontal position, which is the least sensitive position because crystals fall onto the bottom surface of the internal channel. In this way, the crystals cause less disruption in light transmission along the light transmission path and thus are less apparent between the light devices. In a effect a blind spot is created. By tilting the test chamber shown in a horizontal position in FIG. 5, the signal strength can be increased because the crystals fall to the bottom of the internal channel and then slide towards the lowest point where one of the light devices is located. It has been determined that even tilting the light transmission path of the test chamber five degrees (5°) from a horizontal position improves sensitivity. Tilting the test chamber of FIG. 5 to a vertical position ninety degrees (90°), as shown in FIGS. 6–7, should give the maximum sensitivity. However, a ninety degrees (90°) tilt may not be desirable due to other mechanical concerns during use in a vehicle. The consideration of the positioning of the internal channel and light transmission path in relationship to gravity when mounting the test chamber in a vehicle should be considered in all applications of the present invention.

It is envisioned that any of the above setups or other non-disclosed setups using the basic concept could be installed in a fuel tank, near a fuel tank, at a remote location from a fuel tank or as a stand alone hand held unit. Installation in a fuel tank would have to consider the difficulties of installing any type of sensor equipment in a fuel tank. Installation near a fuel tank or at a remote location away from the fuel tank would have to consider the installation of a supply line to the input of the test chamber 3 and a return line from the output of the test chamber 3. Keep in mind that all of the components that make up the basic concept in FIG. 1 do not need to reside at the same location. Use of a stand alone hand held unit would require the installation of some type of access point to provide a supply of fuel from a fuel tank, in order to get a fuel sample into the hand held unit. It is envisioned that there must be a means to move the fuel sample in and out of the test chamber 3, such as a pump or gravity feed system. It is envisioned that there are many ways to get a beam of light in and out of the test chamber 3, which have not been disclosed, but should be consider within the scope of the present invention. It is envisioned that the fuel freezing point monitoring device could be utilized in other vehicle types other than aircraft and a which must also operate in temperature conditions that could freeze the vehicle's fuel supply.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

We claim:

1. A fuel freezing point monitoring device, for determining freezing point of a fuel sample, comprising:

a test chamber having an internal channel for retaining the fuel sample, said internal channel having a length;

an input into said test chamber to allow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along a length of said internal channel of said test chamber and traveling through the fuel sample along said length, said light transmission path having an entrance into said test chamber, an exit out of said test chamber and providing a path for light to travel, said light transmission path being a non-linear path between said entrance and said exit of said light transmission path;

a light source which directs light into said entrance of said light transmission path; and a light detector to detect light level from said light source exiting said exit of said light transmission path.

2. The fuel freezing point monitoring device of claim 1, further including a temperature sensor to measure the temperature of the fuel sample in said test chamber.

3. The fuel freezing point monitoring device of claim 2, further including a data acquisition and control unit to monitor light level from said light detector and monitor fuel sample temperature from said temperature sensor.

4. The fuel freezing point monitoring device of claim 1, wherein said internal channel is in a shape of a "W" and wherein said internal channel includes reflective surfaces along said light transmission path to reflect said light along said "W" shaped internal channel.

5. The fuel freezing point monitoring device of claim 4, further including a temperature sensor to measure the temperature of the fuel sample in said test chamber.

6. The fuel freezing point monitoring device of claim 5, further including a data acquisition and control unit to monitor light level from said light detector and monitor fuel sample temperature from said temperature sensor.

7. The fuel freezing point monitoring device of claim 1, further including a warmer to warm the fuel sample.

8. The fuel freezing point monitoring device of claim 1, wherein the light transmission path between said light source and said light detector is positioned so that the effect of gravity displacing the crystals away from said light transmission path is minimized.

9. A fuel freezing point monitoring device, for determining freezing point of a fuel sample, comprising:

a test chamber having an internal channel for retaining the fuel sample;

an input into said test chamber to allow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along said internal channel of said test chamber and traveling through the fuel sample, said light transmission path having an entrance into said test chamber, an exit out of said test chamber and providing a path for light to travel;

a light source which directs light into said entrance of said light transmission path;

a light detector to detect light level from said light source exiting said exit of said light transmission path; and wherein said fuel freezing point monitoring device is located in a fuel tank.

10. A fuel freezing point monitoring device, for determining freezing point of a fuel sample, comprising:

a test chamber having an internal channel for retaining the fuel sample;

an input into said test chamber to allow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along said internal channel of said test chamber and traveling through the fuel sample, said light transmission path having an entrance into said test chamber, an exit out of said test chamber and providing a path for light to travel;

a light source which directs light into said entrance of said light transmission path;

a light detector to detect light level from said light so exiting said exit of said light transmission path; and wherein said fuel freezing point monitoring device is located in a vehicle and wherein a supply line from a fuel tank is connected to said input.

11. A fuel freezing point monitoring device, for determining freezing point of a fuel sample, comprising:

a test chamber having two straight and separate internal channels for retaining the fuel sample;

an input into said test chamber to allow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along said internal channels of said test chamber and traveling through the fuel sample, said light transmission path having an entrance into said test chamber, an exit out of said chamber and providing a path for light to travel;

a light source which directs light into said entrance of said light transmission path;

a light detector to detect light level from said light source exiting said exit of said light transmission path; and two straight wherein each of said internal channels includes part of said light transmission path; wherein said light source is positioned at said entrance of said light transmission path of a first of said two internal channels; wherein said light detector is positioned at said exit of said light transmission path of a second of said two internal channels; and wherein a light transmission device is linked between said exit of said light transmission path of said first of said two internal channels and said entrance of said light transmission path of said second of said two internal channels, said light transmission device used to transfer said light from said first to said second of said two internal channels.

12. The fuel freezing point monitoring device of claim 11, further including a temperature sensor to measure the temperature of the fuel sample in said test chamber.

13. The fuel freezing point monitoring device of claim 12, further including a data acquisition and control unit to monitor light level from said light detector and monitor fuel sample temperature from said temperature sensor.

14. A fuel freezing point monitoring device, for determining freezing point of a fuel sample, comprising:

a test chamber having a straight internal channel for retaining the fuel sample;

an input into said test chamber to allow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along said internal channel of said test chamber and traveling through the fuel sample, said light transmission path having an entrance into said test chamber, an exit out of said test chamber and providing a path for light to travel;

a light source which directs light into said entrance of said light transmission path;

a light detector to detect light level from said light source exiting said exit of said light transmission path; and wherein said internal channel includes two parallel reflective surfaces, the fuel sample being between said two parallel reflective surfaces; wherein said entrance of said light transmission path is positioned at one end of said test chamber to allow said light from said light source to enter said internal channel at an acute angle and impinge on one of said reflective surfaces to be reflected toward the other of said reflective surfaces; and wherein said reflective surfaces are positioned to reflect said light between said reflective surfaces until said light reaches said exit of said light transmission path at an other end of said internal channel.

15. The fuel freezing point monitoring device of claim 14, further including a temperature sensor to measure the temperature of the fuel sample in said test chamber.

16. The fuel freezing point monitoring device of claim 15, further including a data acquisition and control unit to monitor light level from said light detector and monitor fuel sample temperature from said temperature sensor.

17. A fuel freezing point monitoring device, or determining freezing point of a fuel sample, comprising:

a test chamber having an internal channel for retaining the fuel sample;

an input into said test chamber to slow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along said internal channel of said test chamber and traveling through the fuel sample, said light transmission path having an entrance into said test chamber, an exit out of said test chamber and providing a path for light to travel;

a light source which directs light into said entrance of said light transmission path;

a light detector to detect light level from said light source exiting said exit of said light transmission path; and wherein said light transmission path includes an additional exit along said internal channel to monitor light level which is off set from said light transmission path; and wherein an additional light detector is positioned at said additional exit to monitor light level.

18. The fuel freezing point monitoring device of claim 17, further including a temperature sensor to measure the temperature of the fuel sample in said test chamber.

19. The fuel freezing point monitoring device of claim 18, further including a data acquisition and control unit to monitor light level from said light detectors and monitor fuel sample temperature from said temperature sensor.

20. A fuel freezing point monitoring device, for determining freezing point of a fuel sample, comprising:

a test chamber having an internal channel for retaining the fuel sample;

an input into said test chamber to allow input of the fuel sample into said internal channel from a fuel source;

an output out of said test chamber to allow exiting of the fuel sample in order to properly discharge the fuel sample;

a cooler in thermal contact with said test chamber for cooling the fuel sample in said test chamber;

a light transmission path along said internal channel of said test chamber and traveling through the fuel sample, said light transmission path having an entrance into said test chamber, an exit out of said test chamber and providing a path for light to travel;

a light source which directs light into said entrance of said light transmission path;

a light detector to detect light level from said light source exiting said exit of said light transmission path; and wherein said light transmission path between said light source and said light detector is tilted beyond a horizontal position in relationship to gravity for displacing the crystals properly between said light source and said light detector.

21. A method of monitoring freezing point of fuel comprising:

inputting fuel into an internal channel having a length within a test chamber, whereby fuel is inputted until residual fuel previously retained in the length of the internal channel is removed through an output;

projecting a light into an entrance of a light transmission path which runs through the fuel and along the length of the internal channel;

monitoring light level exiting the light transmission path from an exit of the light transmission path;

projecting the light along a nonlinear path between the entrance and exit of the light transmission path;

cooling the fuel in the internal channel until crystals are formed, so that the light level monitored is reduced;

warming the crystals until no crystals remain, so that the light level monitored increases;

recording temperature at a point where the light level no longer increases, the recorded temperature at the point where the light level no longer increases being the freezing point of the fuel.

22. The method of claim 21, wherein the internal channel is in a shape of a "W" and wherein the internal channel includes reflective surfaces along the light transmission path to reflect the light along the 'W" shaped internal channel.

23. The method of claim 21, wherein the test chamber includes two straight and separate internal channels; wherein each of the internal channels includes the light transmission path; wherein a light source is positioned at the entrance of the light transmission path of a first of the two internal channels; wherein a light detector is positioned at the exit of the light transmission path of a second of the two internal channels: and wherein a light transmission device is linked between the exit of the light transmission path of the first of the two internal channels and the entrance of the light transmission path of the second of the two internal channels, the light transmission device used to transfer the light from the first to the second of the two internal channels.

24. The method of claim 21, wherein the test chamber includes two straight and separate internal channels to provide redundancy in monitoring the freezing point value; wherein each of the internal channels includes the transmission path; wherein a light source is positioned at each entrance of the light transmission paths; and wherein a light detector is positioned at each exit of the light transmission paths.

25. The method of claim 21, wherein the test chamber includes a straight internal channel; wherein the internal channel includes two parallel reflective surfaces, the fuel sample being between the two parallel reflective surfaces; wherein the entrance of the light transmission path is positioned at one end of the test chamber to allow the light from the light source to enter the internal channel at an acute angle and impinge on one of the reflective surfaces to be reflected toward the other of the reflective surfaces; and wherein the reflective surfaces are positioned to reflect the light between the reflective surfaces until the light reaches the exit of the light transmission path at an other end of the internal channel.

26. The method of claim 21, wherein the internal channel includes an additional exit to monitor light level which is off set from the light transmission path; and wherein an additional light detector is positioned at the additional exit to monitor light level, the additional light detector positioned such that the additional light detector sense a reduced level of light when no crystals are present and senses an increase in level of light then crystals are present.

27. The method of claim 21, wherein the internal channel includes two separate light transmission paths within the internal channel to provide redundancy; wherein there is an entrance and exit for each of the two separate transmission paths; wherein the light source is positioned at one of the entrances and an additional light source is positioned at the other of the entrances; and wherein the light detector is positioned at one of the exits and an additional light detector is positioned at the other of the exits.

28. The method of claim 27, wherein the light detectors positioned in relation to the light source of the other light transmission path such that either light detector senses a reduced level of light when no crystals are present and senses an increase in level of light when crystals are present, if the light source from its light transmission path is not functioning.

29. The method of claim 21, wherein the light transmission path between the projection of light and the monitoring of light level is positioned so that the effect of gravity displacing the crystals away from the light transmission path is minimized.

30. The method of claim 29, wherein the light transmission path between the light source and the light detector is tilted beyond a horizontal position in relationship to gravity for displacing the crystals properly between the light source and the light detector.

31. A fuel freezing point monitoring device, for determining freezing point of a fuel sample, comprising:
  a test chamber having an internal channel for retaining the fuel sample, said internal channel having a length;
  an input into said test chamber to allow input of the fuel sample into said internal channel from a fuel source;
  an output out of said test chamber to allow exiting of the fuel sample in order to properly discharge the fuel sample;
  a cooler in thermal contact with said test chamber for cooling the fuel sample in said test chamber;
  at least two separate light transmission paths along said length of said internal channel of said test chamber and traveling through the fuel sample along said length, said light transmission paths each having an entrance into said test chamber, an exit out of said test chamber and providing a path for light to travel;
  a light source which directs light into said entrance of said light transmission path; and
  a light detector to detect light level from said light source exiting said exit of said light transmission path.

32. A fuel freezing point monitoring device, for determining freezing point of a fuel sample, comprising:
  a test chamber having an internal channel for retaining the fuel sample;
  an input into said test chamber to allow input of the fuel sample into said internal channel from a fuel source;
  an output out of said test chamber to allow exiting of the fuel sample in order to properly discharge the fuel sample;
  a cooler in thermal contact with said test chamber for cooling the fuel sample in said test chamber;
  a light transmission path along said internal channel of said test chamber and traveling through the fuel sample, said light transmission path having an entrance into said test chamber, an exit out of said test chamber and providing a path for light to travel;
  a light source which directs light into said entrance of said light transmission path;
  a light detector to detect light level from said light source exiting said exit of said light transmission path; and
  wherein said fuel freezing point monitoring device is located between a supply line to a fuel tank and said fuel tank.

33. A method of monitoring freezing point of fuel comprising:
  inputting fuel into an internal channel having a length within a test chamber, whereby fuel is inputted until residual fuel previously retained in the internal channel is removed through an output;
  providing at least two light transmission paths through fuel along the length of the internal channel, whereby each light transmission path has an entrance and an exit;
  projecting a light into the entrance of at least one of the light transmission paths;
  monitoring light level exiting the light transmission path from an exit of the light transmission path;
  cooling the fuel in the internal channel until crystals are formed, so that the light level monitored is reduced;
  warming the crystals until no crystals remain, so that the light level monitored increases;
  recording temperature at a point where the light level no longer increases, the recorded temperature at the point where the light level no longer increases being the freezing point of the fuel.

34. A method of monitoring freezing point of fuel comprising:
  inputting fuel into an internal channel having a length within a test chamber, whereby fuel is inputted until residual fuel previously retained in the internal channel is removed through an output;
  providing at least two light transmission paths through the fuel along the length of the internal channel, whereby each light transmission path has an entrance and an exit;
  providing a light transmission device to transfer light between the test chamber and other light devices that interact with the fuel along at least one of the light transmission paths;

projecting a light into the entrance of at least one of the light transmission paths;

monitoring light level exiting the light transmission path from an exit of the light transmission path;

cooling the fuel in the internal channel until crystals are formed, so that the light level monitored is reduced;

warming the crystals until no crystals remain, so that the light level monitored increases;

recording temperature at a point where the light level no longer increases, the recorded temperature at the point where the light level no longer increases being the freezing point of the fuel.

35. A method of monitoring freezing point of fuel comprising:

inputting fuel into an internal channel of a test chamber located between a supply line to a fuel tank and the fuel tank, whereby fuel is inputted until residual fuel previously retained in the internal channel is removed through an output;

projecting a light into an entrance of a light transmission path which runs through the fuel in the internal channel;

monitoring light level exiting the light transmission path from an exit of the light transmission path;

projecting the light along a nonlinear path between the entrance and exit of the light transmission path;

cooling the fuel in the internal channel until crystals arc formed, so that the light level monitored is reduced;

warming the crystals until no crystals remain, so that the light level monitored increases;

recording temperature at a point where the light level no longer increases the recorded temperature at the point where the light level no longer increases being the freezing point of the fuel.

36. A method of monitoring freezing point of fuel comprising:

inputting fuel into an internal channel of a test chamber located between a fuel tank and an engine, whereby fuel is inputted until residual fuel previously retained in the internal channel is removed through an output;

projecting a light into an entrance of a light transmission path which runs through the fuel in the internal channel;

monitoring light level exiting the light transmission path from an exit of the light transmission path;

projecting the light along a nonlinear path between the entrance and exit of the light transmission path;

cooling the fuel in the internal channel until crystals are formed, so that the light level monitored is reduced;

warming the crystals until no crystals remain, so that the light level monitored increases;

recording temperature at a point where the light level no longer increases, the recorded temperature at the point where the light level no longer increases being the freezing point of the fuel.

37. A method of monitoring freezing point of fuel comprising:

inputting fuel into an internal channel of a test chamber located between a supply line to a fuel tank and the fuel tank, whereby fuel is inputted until residual fuel previously retained in the internal channel is removed through an output;

projecting a light into an entrance of a light transmission path which runs through the fuel in the internal channel;

monitoring light level exiting the light transmission path from an exit of the light transmission path;

cooling the fuel in the internal channel until crystals are formed, so that the light level monitored is reduced;

warming the crystals until no crystals remain, so that the light level monitored increases;

recording temperature at a point where the light level no longer increases, the recorded temperature at the point where the light level no longer increases being the freezing point of the fuel.

38. A method of monitoring freezing point fuel comprising:

inputting fuel into an internal channel of a test chamber located between a fuel tank and an engine, whereby fuel is inputted until residual fuel previously retained in the internal channel is removed through an output;

projecting a light into an entrance of a light transmission path which runs through the fuel in the internal channel;

monitoring light level exiting the light transmission path from an exit of the light transmission path;

cooling the fuel in the internal channel until crystals are formed, so that the light level monitored is reduced;

warming the crystals until no crystals remain, so that the light level monitored is reduced;

recording temperature at a point where the light level no longer increases, the recorded temperature at the point where the light level no longer increases being the freezing point of the fuel.

39. A method of monitoring freezing point of fuel comprising:

inputting fuel into an internal channel of a test chamber located between a supply line to a fuel tank and the fuel tank, whereby fuel is inputted until residual fuel previously retained in the internal channel is removed through an output;

projecting a light into an entrance of a light transmission path which runs through the fuel in the internal channel;

monitoring light level at a position off set from the light transmission path;

cooling the fuel in the internal channel until crystals are formed, so that the light level monitored is reduced;

warming the crystals until no crystals remain, so that the light level monitored increases;

recording temperature at a point where the light level no longer increases, the recorded temperature at the point where the light level no longer increases being the freezing point of the fuel.

40. A method of monitoring freezing point of fuel comprising:

inputting fuel into an internal channel of a test chamber located between a fuel tank and an engine, whereby fuel is inputted until residual fuel previously retained in the internal channel is removed through an output;

projecting a light into an entrance of a light transmission path which runs through the fuel in the internal channel;

monitoring light level at a position off set from the light transmission path;

cooling the fuel in the internal channel until crystals are formed, so that the light level monitored is reduced;

warming the crystals until no crystals remain, so that the light level monitored increases;

recording temperature at a point where the light level longer increases, the recorded temperature at the point where the light level no longer increases being the freezing point of the fuel.

* * * * *